United States Patent [19]

Feinbloom

[11] Patent Number: 4,988,185
[45] Date of Patent: Jan. 29, 1991

[54] HIGH ADD BIFOCAL SPECTACLES AND METHODS OF PRESCRIBING

[75] Inventor: Richard E. Feinbloom, New York, N.Y.

[73] Assignee: Designs for Vision, Inc., Ronkonkoma, N.Y.

[21] Appl. No.: 253,611

[22] Filed: Oct. 5, 1988

[51] Int. Cl.⁵ .......................... A61B 3/02; A61B 3/04; G02C 7/06

[52] U.S. Cl. .................................. 351/233; 351/168; 351/231

[58] Field of Search ............... 351/227, 228, 229, 230, 351/231, 168, 169, 233, 234, 235, 236

[56]         References Cited
         U.S. PATENT DOCUMENTS

| | | | |
|---|---|---|---|
| 980,070 | 12/1910 | Cowan | 351/228 |
| 1,002,580 | 9/1911 | Griffin | 351/228 |
| 4,407,571 | 10/1983 | Augusto et al. | 351/233 |
| 4,461,550 | 7/1984 | Legendre | 351/169 |

Primary Examiner—Rodney B. Bovernick
Attorney, Agent, or Firm—Arthur L. Plevy

[57] ABSTRACT

A method for prescribing bifocal spectacles for a person having reduced visual acuity includes placing a trial frame on the face of said person in front of his eyes and measuring a far interpupillary distance when said person is viewing a distant object, placing corrective lenses in said frame until said person views said distant object with acuity, placing high plus lenses in said frame for each eye and moving said right and left trial frame sections towards each other while said person is viewing text at a nearer distance and until said person can read said text with binocular vision and then obtaining a near interpupillary distance from said frame and recording said far and near distances with said far prescription and said high plus diopter to employ said recorded data to fabricate bifocal spectacles for said person from said data. The resulting spectacles are also described.

17 Claims, 1 Drawing Sheet

HIGH ADD BIFOCAL SPECTACLES AND METHODS OF PRESCRIBING

BACKGROUND OF THE INVENTION

This invention relates to a method of prescribing bifocal spectacles for the low vision patient and to the resultant spectacles which are then fabricated according to the method.

It is well known in the field of optometry that when working with patients with reduced visual acuity, sometimes referred to as low vision patients, that these patients should be able to read. In regard to accommodating such patients, one employs relative distance magnification to enable such patients to read. Essentially the print or reading material is brought closer to their eyes to create an enlarged retinal image. The practitioner then prescribes high plus lenses to enable such a patient to maintain a clear focus at the near working distance. In any event, there are many considerations which are involved in prescribing such lens systems for patients with reduced visual acuity or low vision patients.

Thus, for example, in addition to the increased accommodative demand, near reading distances require considerably more convergence than are ordinarily employed. For this reason it is generally agreed that binocularity cannot be achieved when the add power of a high plus lens exceeds 12 diopters or more. Thus, in order to reduce the convergence demand practitioners include prism in their prescriptions or simply decenter the lenses to create a prismatic effect. These techniques are accommodated by rules of thumb or employ standard magnification glasses with built in prisms that are commercially available.

In any event, regardless of how the prescription is devised it is absolutely unclear how much convergence is required and it is unclear how to implement or check the final spectacle product to see that it conforms to the prescription generated by the practitioner. As will be explained, an optometrist or practitioner generates a preseciption for a patient with reduced visual acuity which prescription is solely concerned with the measurement of the far interpupillary distance (p.d.). The term for interpupillary distance si sued in this specification to denote the distance between the eyes of the patient indicative of the distance between their center of rotation. This measurement is made by use of a trial frame and when the patient is viewing a distant object The term p.d. is well understood by those skilled in the art and is as defined above. The term "far" p.d. is employed in this specification to denote the conventional p.d. as distinguished from a near p.d. which is part of the teaching of the method of this invention.

Thus, according to prior art techniques and as will be explained, the patient is fitted with a conventional trial frame. Such trial frames are well known and essentially consists of a frame which can accommodate a plurality of trial lenses. The frame can be adjusted to accurately align the frame with the patient's eyes so that the geometrical center distance between the eyes is accurately indicated by adjustment of the frame by means of a calibrated scale located on the frame. This distance is known as the interpupillary distance (p.d.) which is made and measured when the patient is viewing an eye chart where this p.d. is determined at the condition of far viewing to enable the practitioner to record this distance during the examination. The trial frame accommodates various lenses which are inserted into the frame in front of each of the patient's eyes and such corrective lenses are inserted in various combinations until the patient achieves optimum visual acuity indicative of a far or distant prescription.

As one can also ascertain, after a far or a distant prescription is achieved, the practitioner then inserts a high add lens for providing the patient with bifocal viewing. This high add lens is necessary to enable the patient to read at a closer working distance than the distance used for far viewing. As is well known, when high add lenses are used, such as lenses of 4 to 12 diopters one cannot obtain binocular viewing with such lenses due to the extremely short focal lengths. Thus the practitioner or optometrist mathematically computes the amount of base prism required. The base in prism is required to bend the light rays to enable the patient to achieve binocularity at these short focal lengths. Based on the extreme difficulties of such procedures, very few practitioners prescribe for binocularity in the high add range because it is too complicated and cumbersome.

For an example of some of the considerations, reference is made to an article entitled "Determining The Convergence Demand For A Patient Who Reads At A Close Working Distance" by Paul B. Bither published in the American Journal of Optometry and Physiological Optics, Vol. 64, No. 5, pp. 355-360 (May, 1987). This article describes the considerations that a practitioner must involve himself in when attempting to provide comfortable reading spectacles for a patient with reduced visual acuity. The article further contains a bibliography of other pertinent articles which address this problem. As indicated from the article, the author clearly shows and attempts to show the mathematics involved and presents certain charts whereby a practitioner, when obtaining the far interpupillary distance can now determine the amount of base in prism required in regard to various work distances for high add lenses. As the article indicates, while it is clear that the benefits of decentration can be considered, he clearly acknowledges the fact that these techniques are limited.

Thus, one will ascertain by perusing the prior art that a practitioner attempts to mathematically compute the amount of prism required to accommodate a high plus lens needed by a patient to enable the patient to read by means of a bifocal combination. This mathematical computation determines the amount of prism required to enable the patient to achieve binocularity at short focal lengths due to the high add lenses. The prior art attempted are relatively unsuccessful and hence many low vision patients cannot read with binocularity.

It is therefore an object of the present invention to provide a method in which a low vision patient is tested for near distance reading ability utilizing a conventional trial frame and based on the utilization of the trial frame bifocal spectacles, which accommodate both the far distance prescription as well as a near reading prescription, can be fabricated.

It is a further object of this invention to provide a pair of high add bifocal spectacles having unique optical properties to enable a person with reduced visual acuity to be able to both read and to perceive objects at a distance.

It is a further object of the present invention to provide an improved method which a practitioner can employ to determine both the near and distant prescriptions to be employed in providing spectacles for a patient with reduced visual acuity.

SUMMARY OF THE INVENTION

A method of prescribing the optical properties of bifocal spectacles to be worn by a person having reduced visual acuity to enable such person to utilize said spectacles for distant and near vision, comprising the steps of placing a trial frame on the face of said person as said person is viewing a distant object, adjusting said trial frame as placed to determine the distant interpupillary distance between said persons eyes when viewing said distant object, placing lenses in said trial frame to provide said person with a distant lens prescription indicative of optimum visual acuity for distant viewing by said person at said distant interpupillary distance, placing a high add lens in said trial frame of a magnification value enabling said person to view text held at a nearer position than said distant object position, adjusting said trial frame until said person can view said text binocularly at an adjusted near position indicative of a near interpupillary distance, and recording data indicative of said near interpupillary distance together with said distant interpupillary distance together with said distance lens prescription together with said high add magnification value to enable the fabrication of said bifocal spectacles from said recorded data.

BRIEF DESCRIPTION OF THE FIGURES

FIG. is a top plan view showing the patient's eyes in diagrammatic form and necessary to explain the principles of operation of this invention.

DETAILED DESCRIPTION OF INVENTION

Figure 1:
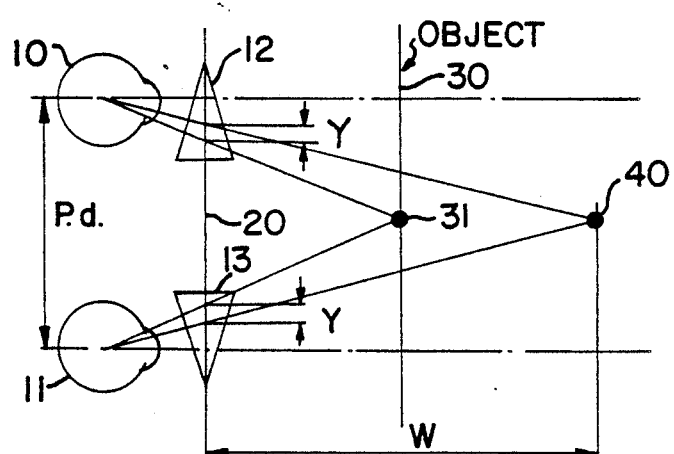

Referring to FIG. 1, there is shown a representation of a patient's eyes designated as 10 and 11. Also shown, in front of the eyes, is a spectacle plane designated as 20. Shown at the spectacle plane are two base in prisms 12 and 13. As briefly explained above, the base in prisms are employed to bend light rays to enable binocular vision at short focal lengths for certain visually handicapped people. Essentially, as seen in FIG. 1, the base prisms 12 and 13 operate to deflect the light rays emanating from the object at point 31. These light rays are deflected by the prism requiring that the eye turn outward. The new line of sight intersects the spectacle plane at a displaced distance Y from the intersection point without the prism. Basically, as shown in FIG. 1, if the prisms 12 and 13 were not employed the line of sight would intersect at point 40 which would be outside the range necessary to enable the handicapped user to view or read the text. If the focusing occurred at point 40, the user of the spectacles could not in any manner achieve a reasonable working distance and hence could not read in the conventional manner.

Figure 2:
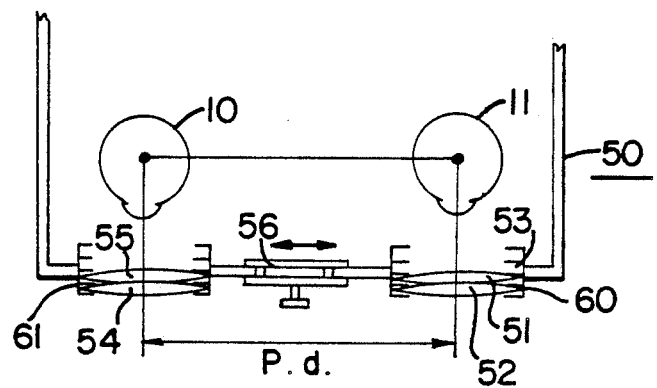
FIG. 2 is a diagrammatic view showing a patient's eyes in conjunction with a trial frame according to the teachings of this invention.

In order to more fully understand the problem, reference is made to FIG. 2. In FIG. 2 there is again shown the patient's eyes 10 and 11 in diagrammatic form. Essentially, as one will understand, present day technology operates to provide a prescription for the patient by the use of a trial frame 50. The trial frame 50, as indicated and shown in FIG. 2, basically is a fully adjustable spectacle frame which has two spectacle carrier section designated as 60 and 61. The sections 60 and 61 operate to accommodate a plurality of lenses which are placed within suitable slots or bins within the trial frame. These lenses, as 51, 52, 55 and 54 are inserted by the practitioner while the trial frame is being accommodated on the face of the patient as held in front of the patient's eyes as in the case of a conventional spectacle frame.

The practitioner then commences to insert lenses into the trial frame, such as lenses 51, 52, 55 and 54. The practitioner, when placing the trial frame on the face of the patient, adjusts the trial frame until he achieves the distant or far p.d. or the distant interpupillary distance. This is done by adjusting the trial frame, as indicated by the arrow, and varying the distance between the spectacle carrying sections 61 and 62 until the distant p.d. of the patient is determined. This occurs when the patient's eyes, as shown in FIG. 2, are in the center or in optical alignment with each of the lens carrying sections 60 and 61 of the trial frame.

This measurement of the distant p.d. is made by the practitioner when the patient, for example, is viewing a remote eye chart. Thus the practitioner reads the distant p.d., designated on FIG. 2 as p.d., by means of the trial frame which automatically provides him with a distant p.d. reading in terms of millimeters. As indicated, the trial frame 50 includes a calibrated scale which automatically gives the reading between the center of frame members 60 and 61 as between the center of rotations of the patient's eyes 10 and 11. Every optometrist is trained and taught to set the trial frame at the distant p.d. which is analogous to the center of rotation of the eyes 10 and 11. With the trial frame set for the distant p.d., the practitioner then proceeds to place lenses in the trial frame to determine the far distance prescription necessary for the particular patient This is done while the patient is viewing a distant eye chart. Hence by placing lenses in the trial frame, such as lenses 51 and 52 and 54 and 55, one determines the prescription for the patient by causing the patient to read from the eye chart. He will change lenses as by removing lenses and adding lenses until the patient satisfactorily views the chart within a desired range and according to his handicap.

After this has been accomplished the practitioner then, based on the number of lenses contained in a trial frame, can determine the prescription necessary for that patient to see at far distances. After this is done, the practitioner then uses another lens which is the high add lens. This lens is also placed in the trial frame and the patient is then given a text or other subject matter to look at at close distance to determine what distance is needed to read. In this manner the patient may need a high add lens of for example between 4 to 12 diopters Let us assume that the high plus lens needed for the bifocal condition is 10 diopters. Once the practitioner selects the necessary high plus add lens, he then determines the final prescription which is sent to a laboratory. As indicated above, based on the use of the high plus add lens, which for example may be 10 diopters, the patient cannot achieve binocular vision. This is due to the fact that the text would have to be held extremely close to the eyes based on the short focal length of the high add lens and therefore the patient cannot achieve binocular vision.

In order to achieve binocular vision, the practitioner must now prescribe a base in prism, such as the prisms 12 and 13 as shown in FIG. 1, to enable the patient to see a single image at the object plane 30 of FIG. 1. The base in prism is necessary to enable the patient to read text, for example, at the point 31 on the object plane 30 of FIG. 1. Thus, what the practitioner now does is to mathematically compute, by means of tables or otherwise, the value of the base in prism to be employed based on the value of the high add lens necessary for this patient to achieve reading ability at the desired plane and based on the patient's interpupillary distance (p.d.).

The practitioner now comes up with the following prescription for the patient. This prescription, for present purposes, will assume that the right and the left eye are exactly the same. Hence, based on the far or the distant prescription, he may specify or write the prescription as follows: +1.00, +1.00, axis 180, add +10 diopters with +12 base in prism each eye. He then specifies that this has been done at a distant p.d. which is equal, for example, to 66 millimeters. It is immediately noted that everything that the practitioner prescribes is related to the distant p.d. which in the above example is 66 millimeters.

In regard to the above, the first designation in the prescription as the +1.00 indicates the spherical lens characteristic. The second, as +1.00 axis 180, indicates a cylindrical lens with the X axis at 180 degrees. The next is the bifocal add lens of 10 diopters with a plus 12 base in prism for each eye. The practitioner then sends the prescription to a laboratory or a spectacle fabricating facility. The facility then makes or prepares a pair of glasses or spectacles, as is conventional, where the top portion of the glass contains the far prescription, which is indicative of the +1.00 spherical lens with the +1.00 X axis 180° cylindrical lens. The bottom portion of the spectacle lens then will contain the bifocal add lens of 10 diopters with +12 base in prism for each eye added over the far prescription. Such bifocal lens arrangements are extremely familiar and one should have no problem in determining the nature of such conventional bifocal spectacles.

The following problems are extremely prevalent in regard to the above-noted procedures. An ordinary lensometer cannot read 10 or 12 diopters of prism. When the prescription arrives in the laboratory and after the spectacles are fabricated, the laboratory takes other lenses which are auxiliary prism lenses and places them in a lensometer to estimate the base in characteristics of the prism as prescribed. These do not work correctly and hence the laboratory cannot make any accurate checks regarding the high add lens with the base in prism characteristic.

When the spectacles or glasses are returned to the practitioner who prescribed the same, he cannot check the lenses as furnished by the laboratory because this involves complicated and difficult operations. Based on the original calculation of the effective base in prism and based on the tables utilized by such practitioners, one cannot in any manner guarantee that the base in prism is selected or fabricated properly. Thus, as one will understand, in modern day optics the high plus area which is necessary to enable a low vision patient to read properly is fabricated and worked on by cut and try techniques. Normally the glasses furnished by the laboratory as prescribed by the practitioner will not enable the patient to read with the use of both eyes and hence he would have to close one eye or the other to attempt to read at a convenient working distance.

As one will understand, and has been acknowledged in the prior art, when a lens has been ordered as a distance correction with a near add, the distance correction is in terms of back focal length while the near add is in terms of front focal length. To verify these aspects the procedures are as follows. The practitioner or laboratory either neutralizes the add ordered with trial lenses at the front surface then measures the back vertex power. This measures the ametropic correction. In other cases, one measures the front vertex power while holding the lenses to neutralize the ametropic correction against the ocular surface of the system. This supposedly is a measure of the near add. To change this dioptic power to effective magnification there is then a division by four. In any event, where the lens power to be measured is beyond the range of the lensometer, the lens to be measured is placed in the instrument and auxiliary concave lenses are placed in contact with the exposed surface. A method of determining the power effect of the auxiliary concave lenses in this location is to read the scale power after removing the microscopic while retaining the concave lens in its original position. The power effect of the auxiliary lens is subtracted algebraically from the scale reading when measuring the microscopic lens.

In those instances where a device will not fit into the lensometer a neutralization or optical bench technique can be employed. As one can see, these tests are extremely difficult and require an excessive amount of time and hence both the laboratory and the practitioner cannot conveniently make such measurements. Thus, as indicated above, the laboratory and the practitioner cannot check the glasses as the procedures are too complicated and therefore it is likely that the patient will not be satisfied by the requisite prescription regarding the near add lens.

Another approach to this problem is to utilize what is indicated in the field as "half eyes." These "half eyes" are provided by the American Optical System Company and come for example in magnifications of 6, 8, 10 and 12 diopters. These half eyeglasses come in standard sizes and having standard amounts of built-in base in prism. The practitioner takes a complete set of the American Optical half eyes with the various diopters and built-in base in prisms and essentially tries these with the patient to determine whether or not the patient can read with these half eyes in conjunction with the trial frame accommodating his distant prescription. If the patient cannot read then then practitioner cannot prescribe a near distant reading lens for the patient.

In the above-cited article of Bither, he gives in tabular form the convergence demand for low vision patients with varying interpupillary distances using the American Optical Series of half eyeglasses with base in prism. He, in that article, indicates how this is accommodated and so on. In any event, as one can ascertain from the above, these techniques have not been successful and hence patients with reduced visual acuity have extreme difficulty in reading and extreme difficulty in reading with the binocular effect.

It has been absolutely ascertained that binocular vision has extreme advantages to patients although its achievement creates extreme problems as above described. The patient feels better psychologically as he feels happier utilizing both eyes. The visual acuity is better and more stable while a wider field of view is available when employing binocular vision and hence the patient can read more efficiently if binocular vision is available. In any event, the above described problems caused by base in prism compensation for short focal length high diopter reading lenses in obtaining binocular vision have not been solved.

As one can understand from the above, all prescriptions, as presently available, are computed from the distant interpupillary distance which is the distance measured between the center of rotations of the patient's eyes while the patient is viewing a remote eye chart and is the distance for example shown in FIGS. 1 and 2 designated as p.d.

Figure 3:
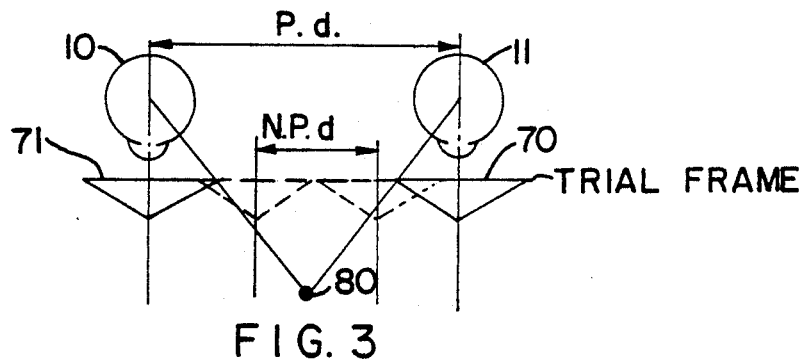
FIG. 3 is a diagrammatic view necessary to explain the method according to this invention.

Referring to FIG. 3, there is shown a schematic necessary to understand the method according to the present invention and which method circumvents the above-noted problems. As seen in FIG. 3, the patient's eyes 10 and 11 are depicted with the interpupillary distance p.d. as in FIG. 2 determined from the trial frame and used to provide the far or distance prescription needed for the patient. The trial frame is shown in schematic form and essentially the lenses, which are selected by the practitioner as for example explained above in conjunction with FIG. 2, are shown in FIG. 3 as 70 and 71. These lenses are spectacle lenses and are generally shown as triangular in section. The reason that the lenses are shown in triangular in cross section is due to the fact that such lenses, which are the combinations of the above-described lenses, are normally convex lenses which result from the combination of spherical and cylindrical lens assemblies. As one will immediately ascertain, most corrective lenses are in fact convex lenses. Thus the convex lenses as 70 and 71 can be roughly approximated by means of the triangles as shown and in order to understand the method taught by the present application.

Essentially the practitioner, when attempting to prescribe for a patient with reduced visual acuity, places the trial frame on the patient's face as indicated in FIG. 2. The practitioner then measures the distant interpupillary distance (p.d.) by adjusting the trial frame and reads the distant p.d. as for example shown in FIG. 3. The practitioner then places lenses in the trial frame until the patient can view the remote eye chart or object with visual acuity and according to his handicap. Thus the lenses as 70 and 71 are indicative of the patient's distant prescription with the p.d. set at the distant p.d.

Now the practitioner again prescribes the proper add lens to enable the patient to read by placing various diopter add lens in the trial frame. Instead of placing prisms in the frame or instead of mathematically computing the base in prism the practitioner now, after specifying lenses 70 and 71, moves the trial frame or decenters the trial frame until the patient sees binocularly at the plane containing point 80. As one can see from FIG. 3, by decentering the trial frame one moves lenses 70 and 71 into the dashed line position. The patient, by rotating his eyes, is now looking through the thin portions of the lenses which essentially are as base in prisms 12 and 13 of FIG. 1. The patient informs the practitioner when he can read text through the decentered lenses 70 and 71 at the plane containing point 80. The patient essentially tells the practitioner that he can now see with both eyes in a binocular manner, as he views an image, and that he is now comfortable at this particular position. At this position the practitioner then reads the scale from the trial frame to arrive at a near p.d. which is designated in FIG. 3 as n.p.d. He then immediately notes or records the near p.d.

This near p.d., as one can ascertain, gives the practitioner the optical center of lenses 70 and 71 at near vision as based on the trial frame which also carries the add lens as for example a 10 diopter lens. Thus, as one can ascertain, the practitioner has measured both the distant p.d. and he now has decentered the trial frame to measure a near p.d. to a position indicated by the patient when the patient achieves binocular reading at the nearer distance. The practitioner then writes the following prescription. He will then specify the far or the distant prescription as indicated above +1.00 which again is a spherical lens surface followed by +1.00 axis 180° which is a cylindrical lens prescription. Then he specifies the add lens as +10 with a near p.d. equal to 54 and with a far p.d. equal to 66. Thus, as one can immediately understand, the practitioner does not in any manner specify to the laboratory the nature of the base in prism for each eye. This automatically has been accommodated by the method, as indicated above, as the near p.d. specifies exactly the proper base in prism for that patient to achieve binocular vision with the 10 diopter high add lens.

When the laboratory receives the above-described prescription, the laboratory is now able to fabricate an exact optical lens assembly for that patient completely indicative of the exact lenses which were accommodated by the trial frame as will be explained in conjunction with FIG. 4.

Figure 4:
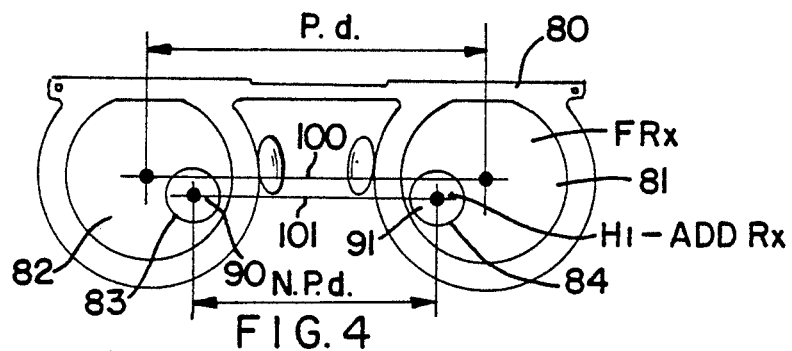
FIG. 4 is a front plan view of a pair of spectacles which have been fabricated according to the methods and teachings of this invention.

Referring to FIG. 4, there is shown a pair of spectacles which have been fabricated according to the method described in FIG. 3. As shown in FIG. 4 a pair of spectacles conventionally contains a typical frame 80. Located and placed within frame 80 are lenses 81 and 82. The lenses 81 and 82 have their optical centers set at the far p.d. which in the above-noted example was 66 millimeters for the patient. Thus the optical centers for lenses 82 and 81 are separated at the far p.d. of 66 millimeters by the frame. The powers of each lens as 81 and 82 are obtained from the prescription and are specified as +1.00 spherical, +1.00 axis 180° cylindrical. This, therefore, completely determines the far prescription or $FR_x$. The optical center of lenses 81 and 82 are on the line 100 and are colinear. The laboratory then marks at a bottom portion or elsewhere of the lenses 81 and 82 the near p.d. separation which in the above-noted example was 54 millimeters. Thus, the two center points 54 millimeters apart near the bottom peripheral edges of the lenses 81 and 82 are marked to determine the n.p.d. When this is done, holes as 83 and 84 are drilled into the lenses 81 and 82. Placed into these apertures are the prescribed high add lenses 90 and 91. As indicated in the above example, the particular patient required a high add lens of +10 diopters. This high add lens of +10 diopters is added over the +1.00 spherical and the +1.00 axis 180° cylindrical lens. This lens is then cut from a standard lens having the +10 add over and placed within apertures 90 and 91. The lenses 90 and 91 have the optical centers on line 101 which is parallel to line 100 and the center of the lenses 90 and 91 are colinear. It automatically has the proper base in prism as the lens is the lens as shown in FIG. 3 in the dashed line position. From this lens the lenses as 90 and 91 are automatically known due to the fact that one moved the p.d. from 66 to 54 using the far distance lenses with the added high add lenses. Hence, one automatically obtains the proper base in prism. Thus the base in prism is automatically derived from the effective difference between the far p.d. and the near p.d. as determined by the practitioner from adjustment of the trial frame as adjusted with the patient's input.

It is also noted that for every 10 diopters that are moved one millimeter, one has an effective base prism of 1 diopter. Thus lenses 90 and 91 have the exact add on magnification required by the patient and are in fact positioned exactly where the patient, as in FIG. 3, was able to read with binocular vision as for example at the plane containing point 80. Hence there is absolutely no problem in accommodating the proper base in prism for the patient by using the above-noted method.

As one can also understand, both the laboratory and the practitioner can easily check both the far distant lenses 81 and 82 in regard to their prescribed values as well as lenses 90 and 91 in regard to the near interpupillary distance and the required magnification which is in that example a +10 add over the +1.00 spherical, +1.00 axis 180 cylindrical lens. Hence the above-described technique, as well as the spectacles thus provided as shown in FIG. 4, eliminate the above-described problems associated with the prior art and enable both the practitioner and the laboratory to accurately provide low vision patients the ability to read with binocularity at the proper magnification. The spectacles as shown in FIG. 4 contain both the proper distant prescription as well as the proper near prescription enabling that patient to optimumly utilize the spectacles for both far and near vision.

Thus, according to this technique, the practitioner now has to record three things. First, he now measures the distant p.d. as indicated and utilizing the trial frame places lenses within the trial frame enabling the patient to see optimumly at the distant p.d. and records the distant prescription. Then he adds a high add lens between 4 to 12 diopters. He now moves the trial frame to decrease the interpupillary distance as the patient is holding reading matter at a given plane such as that containing point 80 of FIG. 3. This plane is selected at a reasonable working distance for the patient. When the patient indicates that he sees with binocular vision the practitioner then records the reading on the trial frame specifying the near p.d. This is then utilized in the prescription as sent to the laboratory. Thus the prescription sent to the laboratory will contain the far prescription as completely determining lenses 81 and 82 as well as the far p.d. namely to describe the centers between lenses 81 and 82. The prescription will also contain the magnitude of the high add lens, as for example +10 diopters plus the near pupillary distance (n.p.d.) to enable the laboratory to drill the adequate holes based on the near p.d. dimensions and to provide lenses as 90 and 91 to be inserted into the apertures to therefore enable the patient again to see with binocularity without in any manner calculating or attempting to calculate the base in prism as this is automatically achieved.

The diameters of lenses 81 and 82 are approximately between 60-75 millimeters with the diameters of lenses 90 and 91 between 20-32 millimeters. These dimensions are only by way of example and other dimensions will suffice as well.

What is claimed is:

1. A method of prescribing the optical properties of bifocal spectacles to be worn by a person having reduced visual acuity to enable such person to utilize said spectacles for distant and near vision, comprising the steps of:
    placing a trial frame on the face of said person as said person is viewing a distant object;
    adjusting said trial frame as placed to determine the distant interpupillary distance between said persons eyes when viewing said distant object;
    placing lenses in said trial frame to provide said person with a distant lens prescription indicative of optimum visual acuity for distant viewing by said person at said distant interpupillary distance;
    placing a high add lens in said trial frame of a magnification value enabling said person to view text held at a nearer position than said distant object position;
    adjusting said trial frame until said person can view said text binocularly at an adjusted near position indicative of a near interpupillary distance; and
    recording data indicative of said near interpupillary distance together with said distant interpupillary distance together with said distant lens prescription together with said high add magnification value to enable the fabrication of said bifocal spectacles from said recorded data.

2. The method according to claim 1 further including fabricating bifocal spectacles from said recorded data comprising the steps of:
    placing lenses indicative of said distant lens prescription in a spectacle frame with the center of said lenses separated in said frame at said distant interpupillary distance;
    forming a colinear hole in each of said lenses in said frame with the centers of said holes separated in said frame by said near interpupillary distance; and
    placing lenses in said holes having a prescription indicative of said distant lens prescription added over said high add magnification.

3. The method according to claim 1 wherein said high add lens has a magnification between 4-12 diopters.

4. The method according to claim 1 wherein said distant lens prescription contains a spherical and/or cylindrical lens component.

5. A method of deriving a prescription for bifocal spectacles to be worn by a person having reduced visual acuity to enable said person to utilize said spectacles for distant and near viewing, comprising the steps of:
    measuring the distant interpupillary distance between the eyes of said person when said person is viewing a distant object with said distance indicative of the distance between the centers of rotation of said person's eyes;
    placing corrective lenses in front of said patient's eyes at a spectacle reference plane to formulate a lens prescription for said person enabling said person to view said distant object with optimum acuity at said distant interpupillary distance;
    placing high plus lenses in the path of said corrective lenses of a diopter value indicative of a given magnification to enable said person to read text at some given nearer distance;
    moving said high plus lens and said corrective lenses toward each other along the same axis by given amounts while said person views said text at said nearer distance and to move said lenses until said person can binocularly view said text with visual acuity at said nearer distance to enable reading of the same;
    measuring the distance between the center of said lenses as moved when said person can read said text to provide a near interpupillary distance; and
    recording data indicative of said distant interpupillary distance, said lens prescription, said diopter value of said high plus lens and said near interpupillary distance to enable the fabrication of said bifocal spectacles from said recorded data.

6. The method according to claim 5 wherein the steps of measuring the distant interpupillary distance includes placing a trial frame on the face of said person and adjusting said trial frame while the eyes of said person are viewing said distant object to obtain said interpupillary distance from said frame.

7. The method according to claim 6 wherein the step of placing corrective lenses in front of the eyes of said person includes placing corrective lenses in said trial frame at said distant interpupillary distance.

8. The method according to claim 7 wherein the step of placing said high plus lens includes placing said high plus lens in said trial frame as accommodating said corrective lenses.

9. The method according to claim 8 wherein the step of moving said corrective and high plus lenses includes adjusting said trial frame in a direction to move said accommodated lenses indicative of the right and left eye towards each other and stopping said movement when said person reads binocularly at an position indicative of said near interpupillary distance.

10. The method according to claim 5 further including fabricating bifocal spectacles from said recorded data, comprising the steps of:
placing lenses indicative of said distant lens prescription in a spectacle frame with the center of said lenses separated in said frame at said distant interpupillary distance;
forming an aperture in each lens along a line parallel to a line joining the center of said lenses, with the centers of said aperture colinear and separated by said near interpupillary distance; and
inserting lenses in said aperture each having a prescription indicative of said distant lens prescription added over said diopter value of said high plus lens.

11. The method according to claim 5 wherein said high plus lens is between 4-12 diopters.

12. The method according to claim 5 wherein said corrective lens has a cylindrical and spherical component and is generally a convex lens.

13. Bifocal spectacles for persons with reduced visual acuity, comprising:
a spectacle frame having first and second lenses positioned in the right and left half lens accommodating areas of said frame with each lens indicative of a far distance prescription for said person and having the centers of said lenses as held in said frame separated by the interpupillary distance of said person's eyes when viewing a distant object, each of said lenses having a colinear aperture of an appreciable smaller diameter than said lens with the center of said apertures separated in said frame by a near interpupillary distance determined for said person when said person moves his eyes to a reading position where said person can view text at a near distance with binocularity;
a third and a fourth lens each located in one of said apertures and each having a prescription indicative of said far distance prescription added over a given diopter high plus lens, whereby said person can move his eyes to view through said third and fourth lenses enabling said person to binocularly view text at said near distance.

14. The bifocal spectacles according to claim 13 wherein said given diopter high plus lens has a diopter value between 4-12.

15. The bifocal spectacles according to claim 13 wherein said near interpupillary distance is the distance as measured by a trial frame wherein said patient can read text with binocularity when said trial frame is accommodating said far distance prescription with said high plus lens as said trial frame is moved from said far interpupillary distance.

16. The bifocal spectacles according to claim 15 wherein said interpupillary distance is measured by a trial frame placed on the face of said person as said person is viewing a distant object.

17. The bifocal spectacles according to claim 13 wherein the diameter of said third and fourth lenses is about one-third the diameter of said first and second lenses.

* * * * *